(12) United States Patent
Grandfield et al.

(10) Patent No.: US 7,717,864 B1
(45) Date of Patent: May 18, 2010

(54) COMPOSITE GUIDEWIRE WITH DRAWN AND FILLED TUBE CONSTRUCTION

(75) Inventors: Ryan Grandfield, Murrieta, CA (US); Mark T. Richardson, Escondido, CA (US); Peter D'Aquanni, Murrieta, CA (US); Wayne E. Cornish, Fallbrook, CA (US); Jonathan M. Howland, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1026 days.

(21) Appl. No.: 10/419,577

(22) Filed: Apr. 21, 2003

Related U.S. Application Data

(63) Continuation-in-part of application No. 09/470,874, filed on Dec. 22, 1999, now Pat. No. 7,645,242, which is a continuation-in-part of application No. 09/224,453, filed on Dec. 31, 1998, now Pat. No. 6,142,975.

(51) Int. Cl.
*A61B 5/00* (2006.01)
(52) U.S. Cl. ............... 600/585; 604/524; 604/526; 600/434
(58) Field of Classification Search ........... 604/170.01, 604/524–530; 600/585, 434, 114
See application file for complete search history.

(56) References Cited

U.S. PATENT DOCUMENTS

| | | | |
|---|---|---|---|
| 4,538,622 A | 9/1985 | Samson et al. | |
| 4,748,986 A | 6/1988 | Morrison et al. | |
| 4,818,486 A * | 4/1989 | Rothman et al. | ............ 420/442 |
| 4,917,104 A | 4/1990 | Rebell | |
| 4,925,445 A | 5/1990 | Sakamoto et al. | |
| 5,069,217 A | 12/1991 | Fleischhacker, Jr. | |
| 5,069,226 A | 12/1991 | Yamauchi et al. | |
| 5,135,503 A | 8/1992 | Abrams | |
| 5,171,383 A | 12/1992 | Sagaye et al. | |
| 5,213,111 A | 5/1993 | Cook et al. | |
| 5,230,348 A | 7/1993 | Ishibe et al. | |
| 5,238,004 A | 8/1993 | Sahatjian et al. | |
| 5,253,653 A | 10/1993 | Daigle et al. | |
| 5,341,818 A | 8/1994 | Abrams et al. | |
| 5,345,945 A | 9/1994 | Hodgson et al. | |
| 5,411,476 A * | 5/1995 | Abrams et al. | ........... 604/95.01 |
| 5,506,059 A | 4/1996 | Robbins et al. | |
| 5,520,194 A | 5/1996 | Miyata et al. | |
| 5,588,443 A | 12/1996 | Davidson | |
| 5,607,463 A | 3/1997 | Schwartz et al. | |
| 5,628,787 A | 5/1997 | Mayer | |
| 5,630,840 A | 5/1997 | Mayer | |

(Continued)

FOREIGN PATENT DOCUMENTS

WO  WO 96/25969 A2  8/1996

(Continued)

*Primary Examiner*—Nicholas D Lucchesi
*Assistant Examiner*—Laura A Bouchelle
(74) *Attorney, Agent, or Firm*—Fulwider Patton LLP

(57) ABSTRACT

The present invention is directed to an intracorporeal device, preferably a guidewire, and method for making the device. The guidewire of the present invention is formed, at least in part, of a composite elongate core formed, at least in part, of precipitation hardened material. The elongate core members of the present invention will have an ultimate tensile strength and modulus of elasticity greater than the same for an identically dimensioned elongate member formed from superelastic NITINOL alone.

18 Claims, 3 Drawing Sheets

U.S. PATENT DOCUMENTS

| | | | |
|---|---|---|---|
| 5,636,641 A * | 6/1997 | Fariabi | 600/585 |
| 5,636,642 A | 6/1997 | Palermo | |
| 5,637,089 A * | 6/1997 | Abrams et al. | 604/95.01 |
| 5,647,858 A | 7/1997 | Davidson | |
| 5,664,580 A | 9/1997 | Erickson et al. | |
| 5,695,111 A * | 12/1997 | Nanis et al. | 228/206 |
| 5,720,300 A * | 2/1998 | Fagan et al. | 600/585 |
| 5,725,570 A | 3/1998 | Heath | |
| 5,725,572 A | 3/1998 | Lam et al. | |
| 5,733,326 A | 3/1998 | Tomonto et al. | |
| 5,749,837 A | 5/1998 | Palermo et al. | |
| 5,776,080 A * | 7/1998 | Thome et al. | 600/585 |
| 5,824,056 A | 10/1998 | Rosenberg | |
| 5,824,077 A | 10/1998 | Mayer | |
| 5,827,201 A * | 10/1998 | Samson et al. | 600/585 |
| 5,843,166 A | 12/1998 | Lentz et al. | |
| 5,885,381 A | 3/1999 | Mitose et al. | |
| 5,891,191 A | 4/1999 | Stinson | |
| 5,951,793 A | 9/1999 | Mitose et al. | |
| 5,984,878 A | 11/1999 | Engelson | |
| 6,068,623 A | 5/2000 | Zadno-Azizi et al. | |
| 6,132,389 A | 10/2000 | Cornish et al. | |
| 6,142,975 A | 11/2000 | Jalisi et al. | |
| 6,217,567 B1 | 4/2001 | Zadno-Azizi et al. | |
| 6,245,030 B1 | 6/2001 | DuBois et al. | |
| 6,296,616 B1 | 10/2001 | McMahon | |
| 6,432,066 B1 * | 8/2002 | Ferrera | 600/585 |
| 6,610,155 B2 * | 8/2003 | Pike et al. | 148/675 |
| 2002/0082681 A1 * | 6/2002 | Boylan et al. | 623/1.19 |

FOREIGN PATENT DOCUMENTS

| | | | |
|---|---|---|---|
| WO | WO 9625969 A2 * | 8/1996 | |
| WO | WO 98/22024 | * | 5/1998 |
| WO | WO 98/22024 A1 | 5/1998 | |
| WO | WO 99/46109 A1 | 9/1999 | |
| WO | WO 00/32265 A1 | 6/2000 | |

* cited by examiner

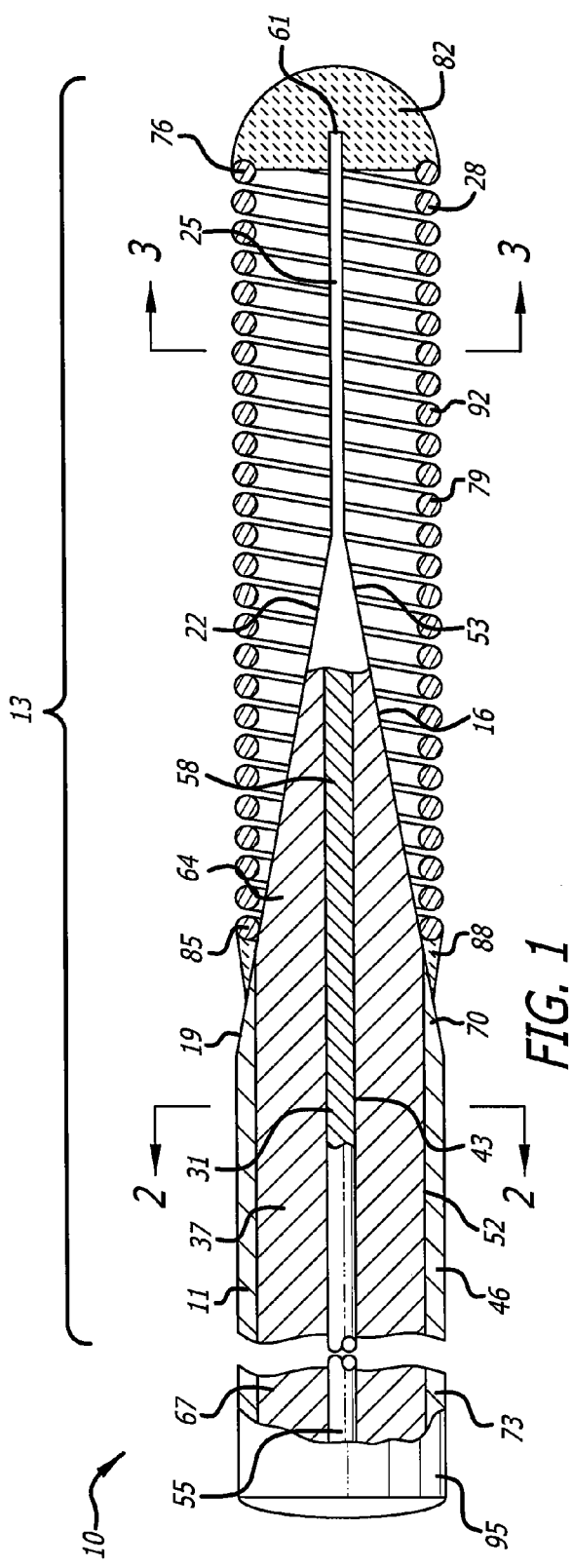
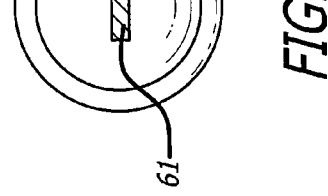
FIG. 1
FIG. 3
FIG. 2

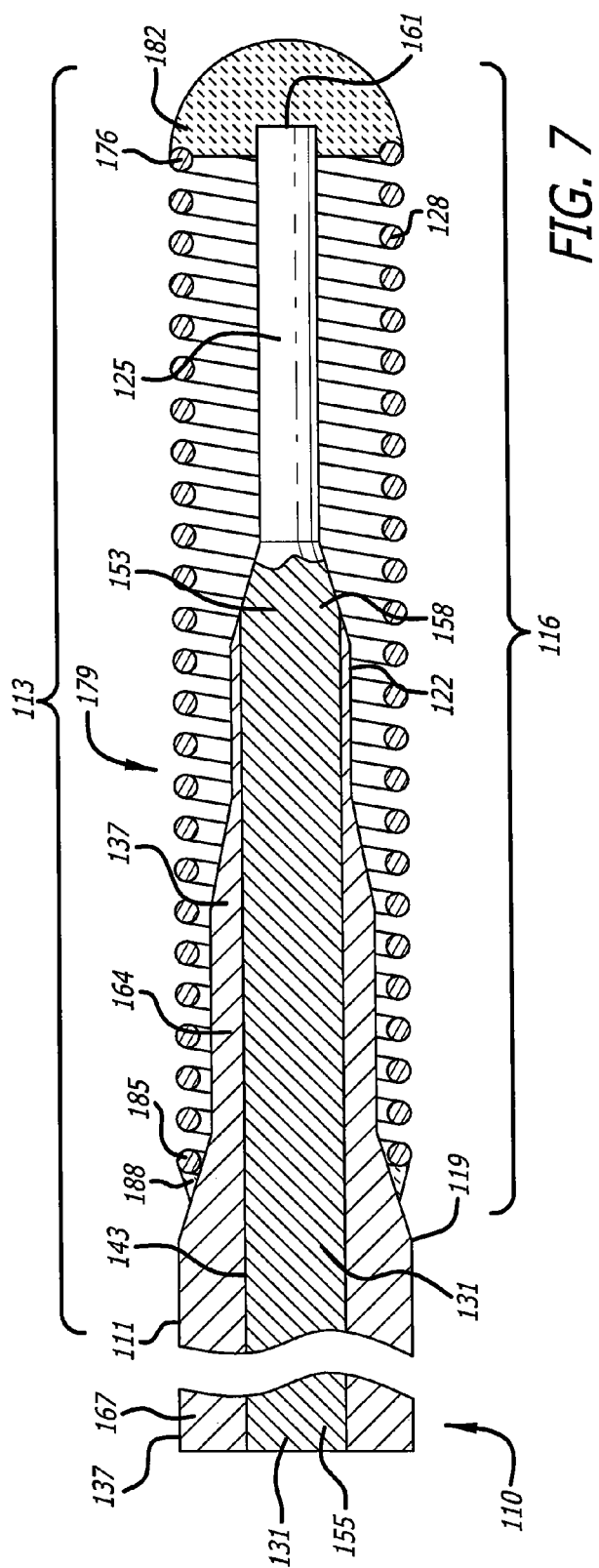
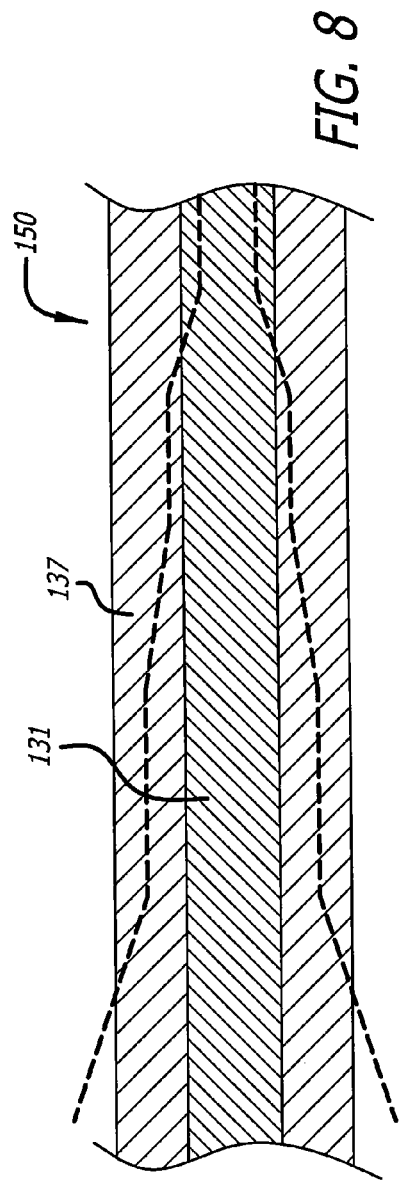

COMPOSITE GUIDEWIRE WITH DRAWN AND FILLED TUBE CONSTRUCTION

CROSS-REFERENCE TO RELATED APPLICATIONS

This application is a continuation-in-part of U.S. patent application Ser. No. 09/470,874, now U.S. Pat. No. 7,645,242 filed on Dec. 22, 1999, which is a continuation-in-part of U.S. patent application Ser. No. 09/224,453, now U.S. Pat. No. 6,142,975 filed on Dec. 31, 1998, whose contents are herein incorporated by reference in their entirety.

FIELD OF INVENTION

This invention relates to the field of guidewires for advancing intraluminal devices such as stent delivery catheters, balloon dilation catheters, atherectomy catheters and the like within body lumens.

BACKGROUND OF THE INVENTION

Conventional guidewires for angioplasty and other vascular procedures usually comprise an elongated core member with one or more tapered sections near the distal end thereof and a flexible body such as a helical coil disposed about the distal portion of the core member. A shapeable member, which may be the distal extremity of the core member or a separate shaping ribbon which is secured to the distal extremity of the core member extends through the flexible body and is secured to a rounded tip at the distal end of the flexible body.

In a typical coronary procedure, a guiding catheter having a preformed distal tip is percutaneously introduced into a patient's peripheral artery, e.g., femoral or brachial artery, by means of a conventional Seldinger technique and advanced therein until the distal tip of the guiding catheter is seated in the ostium of a desired coronary artery. A guidewire is positioned within an inner lumen of a dilation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilation catheter having an inflatable balloon on the distal portion thereof is advanced into the patient's coronary anatomy over the previously introduced guidewire until the balloon of the dilation catheter is properly positioned across the lesion. Once in position across the lesion, the procedure is performed.

A requirement for guidewires is that they have sufficient column strength to be pushed through a patient's vascular system or other body lumen without kinking. However, guidewires must also be flexible enough to avoid damaging the blood vessel or other body lumen through which they are advanced. Efforts have been made to improve both the strength and flexibility of guidewires to make them more suitable for their intended uses, but these two properties are for the most part, diametrically opposed to one another in that an increase in one usually involves a decrease in the other.

Further details of guidewires, and devices associated therewith for various interventional procedures can be found in U.S. Pat. No. 4,748,986 (Morrison et al.); U.S. Pat. No. 4,538,622 (Samson et al.); U.S. Pat. No. 5,135,503 (Abrams); U.S. Pat. No. 5,341,818 (Abrams et al.); and U.S. Pat. No. 5,345,945 (Hodgson et al.); all of which are incorporated herein in their entirety by reference.

Some guidewires have been formed from a superelastic alloy such as a NITINOL (nickel-titanium or NiTi) ally, to achieve both flexibility and strength. When stress is applied to NITINOL alloy exhibiting superelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation.

If the load on the specimen is removed before any permanent deformation has occurred, the martensitic phase of the specimen will elastically recover and transform back to the austenite phase. The reduction in stress first causes a decrease in strain. As stress reduction reaches the level at which the martensite phase transforms back into the austenite phase, the stress level in the specimen will remain essentially constant until the transformation back to the austenite phase is complete, i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity. These properties to a large degree allow a guidewire core of a superelastic material to have both flexibility and strength.

While the properties of the guidewire formed of the superelastic material were very advantageous, it was found that the guidewires and guiding members formed of materials having superelastic characteristics did not have optimum push and torque characteristics.

Furthermore, although nickel-titanium guidewires are useful and valuable to the medical field, a distinct disadvantage with nickel-titanium guidewires is the fact that they are not sufficiently radiopaque as compared to a comparable structure including gold or tantalum. Radiopacity permits the cardiologist or physician to visualize the procedure involving the guidewire through use of fluoroscopes or similar radiological equipment. Good radiopacity is therefore a useful feature for nickel-titanium guidewires to have.

Radiopacity can be improved by increasing the thickness of the nickel-titanium guidewire. But increasing core diameter detrimentally affects the flexibility of the guidewire, which is a quality necessary for accessibility in a tortuous anatomy. Also, nickel-titanium is difficult to machine and large diameter guidewires exacerbate the problem. Radiopacity can further be improved through coating processes such as sputtering, plating, or co-drawing gold or similar heavy metals onto the guidewire. These processes, however, create complications such as material compatibility, galvanic corrosion, high manufacturing cost, coating adhesion or delamination, biocompatibility, etc. Radiopacity can also be improved by alloy addition. One specific approach is to alloy the nickel-titanium with a ternary element.

SUMMARY OF THE INVENTION

The present invention is directed to an intracorporeal device, preferably a guidewire, and method for making the device. The guidewire of the present invention is formed, at least in part, of a composite elongate core member formed, at least in part, of precipitation hardened material. The elongate core members of the present invention will have an ultimate tensile strength and modulus of elasticity greater than the same for an identically dimensioned elongate member formed from superelastic NITINOL alone.

Preferably, the composite elongate core member has a modulus of elasticity of at least $9\times10^6$ psi, more preferably, at least $12\times10^6$ psi, and most preferably, at least $15\times10^6$ psi.

Preferably, the composite elongate core member has an ultimate tensile strength of at least 150 ksi, more preferably, at least 180 ksi, and most preferably, at least 200 ksi.

In one embodiment, the precipitation hardened material is formed from a material comprising at least two materials selected from the group consisting of nickel, cobalt, molybdenum, chromium, tungsten, and iron.

In one embodiment, the precipitation hardened material is formed from a precipitation hardenable stainless steel. Preferably, the precipitation hardenable stainless steel is chromium-nickel based single stage martensitic precipitation hardenable stainless steel. In another embodiment, the precipitation hardenable stainless steel is essentially nickel free.

In another embodiment, the precipitation hardened material is formed from a cobalt based alloy. In one embodiment the cobalt based alloy further includes nickel, molybdenum and chromium while in another embodiment it further includes less than about 10% by wt. iron.

In one preferred embodiment, the composite elongate core member has an inner core element and a first layer portion disposed at least in part about the inner core element, the inner core element and the first layer portion being formed of different materials. In an embodiment, the inner core element and the first layer portion are independently formed from superelastic NITINOL and precipitation hardenable material. In another embodiment, the composite elongate core member further includes a second layer portion disposed at least in part about the first layer portion and formed of a material similar to the inner core element material.

In a preferred embodiment, the composite elongate core member includes a distal segment having a distally tapered section with proximal and distal portions, and a distal flexible section, the inner core element being at least partially exposed at the distal flexible section of the distal segment of the composite elongate member.

In yet another embodiment, the first layer portion is formed from superelastic NITINOL and further includes a ternary element selected from the group of chemical elements consisting of iridium, platinum, gold, rhenium, tungsten, palladium, rhodium, tantalum, silver, ruthenium, and hafnium. In one embodiment, the superelastic NITINOL includes, preferably, 42.8 atomic percent nickel, 49.7 atomic percent titanium, and 7.5 atomic percent platinum.

As a result, this embodiment is highly radiopaque as compared to an identical structure made of medical grade stainless steel that is coated with a thin layer of gold. From another perspective, for a given guidewire having a certain level of radiopacity, the same level of radiopacity is maintained by the present invention guidewire with a reduction in core diameter.

To achieve the sufficient degree of radiopacity while maintaining the superelastic engineering properties of binary nickel-titanium, the radiopaque guidewire of this embodiment includes, preferably, platinum whose atomic percent is greater than or equal to 2.5 and less than or equal to 15. In an alternative embodiment, the nickel-titanium is alloyed with palladium whose atomic percent is greater than or equal to 2.5 and less than or equal to 20. With such compositions, the stress-strain hysteresis curve of the radiopaque nitinol alloy closely approximates the idealized stress-strain hysteresis curve of binary nickel-titanium. It is contemplated that minor amounts of a quaternary element, for example, iron, may be added to further enhance the alloy's formability or its thermomechanical properties.

As is known in the art, many materials used for guidewire construction have desirable mechanical properties, but are difficult to assemble to other guidewire components using conventional technology such as soldering or use of polymer adhesives due to inherent surface properties such as tenacious oxide layers. The construction of guidewires according to the present invention allows the use of materials which have poor bondability or solderability.

The present invention allows for the design of a guidewire with a unitary core, rather than a core with proximal and distal segments joined together. Additionally, the core members of the present invention may be used with other wire designs to create guidewires with improved superelasticity and kink-resistance.

The present invention further contemplates a method for providing a radiopaque guidewire having a NITINOL first layer portion, the first layer portion including a ternary element and the inner core element formed of precipitation hardenable material. The method entails providing a tube which is formed of a superelastic nickel-titanium alloy, the alloy further including a ternary element selected from the group of chemical elements consisting of iridium, platinum, gold, rhenium, tungsten, palladium, rhodium, tantalum, silver, ruthenium, and hafnium; forming a tube that is highly radiopaque. The step of providing the tube includes melting nickel, titanium, and the ternary element and cooling the mixture to form an alloy ingot, hot forming the alloy ingot, hot or cold forming the alloy ingot into a cylinder, drilling the cylinder to form tubing, cold drawing the tubing, and annealing the tubing. A conventional drawn filled tube technique known in the art is used to provide the layering of the NITINOL tube having the ternary element over the core of precipitation hardenable material.

BRIEF DESCRIPTION OF THE DRAWINGS

FIG. 1 is a longitudinal cross sectional view of a guidewire embodying features of the invention.

FIG. 2 is a transverse cross sectional view of the guidewire of FIG. 1 taken along line 2-2.

FIG. 3 is a transverse cross sectional view of the guidewire of FIG. 1 taken along line 3-3.

FIG. 7 is a longitudinal cross-sectional view of an alternative guidewire design.

FIG. 8 is a cross-sectional view of the as-received drawn filled tube core composition for the guidewire illustrated in FIG. 7.

DETAILED DESCRIPTION OF THE INVENTION

Figure 5:
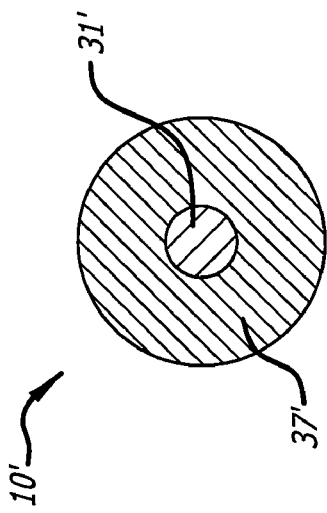
FIG. 5 is a transverse cross sectional view of an alternative guidewire embodying another configuration.

FIGS. 1, 2 and 3 illustrate features of a guidewire 10 embodying the present invention. A composite elongate core member 11 has a distal segment 13 having a distally tapered section 16 with a proximal portion 19, a distal portion 22, and a distal flexible section 25 at a distal end 28 of the guidewire 10 for negotiating the guidewire 10 through the patient's vasculature without causing injury thereto. The distally tapered section 16 can be adjusted in length, taper angle and cross sectional shape to achieve the desired flexibility and performance characteristics for the guidewire 10.

The elongate core member 11 has an inner core element 31 formed from a precipitation hardenable material, a first layer portion 37 formed from a superelastic material disposed on an outer surface 43 of the inner core element 31, and a second layer portion 46 formed from precipitation hardenable material disposed on an outer surface 52 of the first layer portion 37. The inner core element 31 is at least partially exposed at the distal flexible section 25 of the distal segment 13 of the composite elongate member 11. The inner core element 31 may also be exposed at a distal end 53 of the distal portion 22. The first layer portion 37 is at least partially exposed at the distal portion 22 of the distally tapered section 16 of the distal segment 13 of the composite elongate core member 11.

In FIG. 1, the first layer portion 37 and second layer portion 46 are shown as smooth continuous layers. The inner core element 31 has a proximal section 55, a distal section 58 and a distal end 61. The first layer portion 37 has a distal section 64 and a proximal section 67. The second layer portion 46 has a distal section 70 and a proximal section 73.

The distal end 61 of the inner core element 31 is secured to a distal end 76 of a flexible body 79 by a first body of solder 82. A proximal end 85 of the flexible body 79 is secured to the distal section 70 of the second layer portion 46 with a second body of solder 88. Although a single distally tapered section 16 is shown, the distal segment 13 of the elongate core member 11 may have two or more such tapered segments which may or may not be separated by segments of substantially constant diameter. The flexible body 79 is disposed partially about the distally tapered section 16 of the distal segment 13 of the elongate core member 11. The distal flexible section 25 is shown as a flattened portion of the exposed inner core element 31, however, the distal flexible section 25 can have a round cross section, or any other suitable configuration.

The flexible body 79 may be any flexible material such as a helical coil or a polymer jacket, or the like. Polymers suitable for forming the flexible body 79 include, but are not limited to, polyimide, polyethylene, polyurethane, tetrafluoroethylene (TFE), polytetrafluoroethylene (PTFE), expanded polytetrafluoroethylene (PTFE), and other similar materials. The flexible body 79 in the form of a helical coil 92 (as shown in FIG. 1) may be formed of a suitable radiopaque material such as tantalum, gold, iridium, platinum or alloys thereof or formed of other material such as stainless steel and coated with a radiopaque material such as gold. The wire from which the coil 92 is made generally has a transverse diameter of about 0.001 to about 0.004 inch, preferably about 0.002 to about 0.003 inch. Multiple turns of a distal portion of coil 92 may be expanded to provide additional flexibility. The flexible body 79 may have transverse dimensions about the same as a proximal section 95 of the elongate core member 11. The flexible body 79 may have a length of about 2 to about 40 cm or more, but typically will have a length of about 2 to about 10 cm.

The inner core element 31, at an untapered region such as the proximal section 95 of the elongate core member 11, has a nominal transverse dimension of up to about 0.010 inches, preferably, about 0.003 to about 0.01 inches, and more preferably, about 0.003 to about 0.006 inches. The first layer portion 37 and second layer portion 46, at an untapered region such as the proximal section 95 of the elongate core member 11, each have a nominal wall thickness of up to about 0.015 inches, preferably, about 0.0005 to about 0.01 inches, and more preferably, about 0.001 to about 0.003 inches. Although the inner core element 31 is shown as solid, the inner core element 31 may also be hollow with a lumen extending longitudinally therethrough (not shown) for delivery of diagnostic or therapeutic agents, such as radioactive therapy agents or angiogenic growth factors or the like; or for advancement of elongated medical devices into a patient's vasculature.

The inner core element 31 and the second layer portion 46 may both be formed of precipitation hardened material formed from precipitation hardenable material, with the first layer portion 37 being formed from a superelastic material such as superelastic NITINOL. However, as discussed below, other configurations may also be employed in the practice of the invention.

Figure 4:
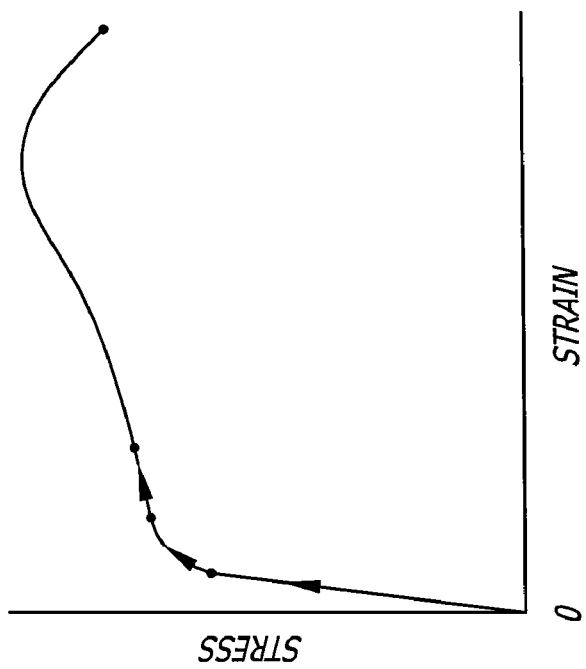
FIG. 4 is a diagrammatic illustration of a stress-strain curve.

A significant aspect of the invention resides in forming the composite elongate core member 11, at least in part, from precipitation hardenable material so that the ultimate tensile strength ($\sigma_{uts}$) and tensile yield strength ($\sigma_{ys}$) of the composite (FIG. 4) are raised to enhance the elastic strength and operability of the guidewire, as compared to an elongate core member formed of superelastic NiTi alone.

In an embodiment, features of which are illustrated in FIG. 5 and wherein like references refer to like parts, the guidewire 10' has an inner core element 31' formed from precipitation hardenable material (e.g., precipitation hardenable stainless steel) and a first layer portion 37' formed from superelastic material (e.g., superelastic NITINOL).

Figure 6:
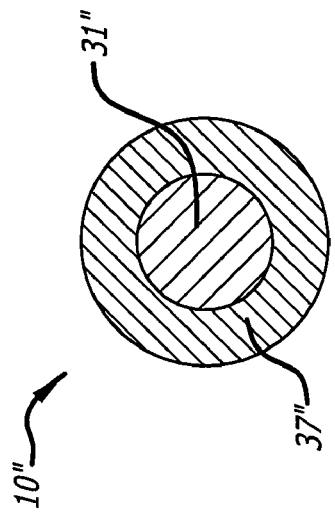
FIG. 6 is a transverse cross sectional view of another alternative guidewire embodying another configuration.

In another embodiment, features of which are illustrated in FIG. 6 and wherein like references refer to like parts, the guidewire 10" has an inner core element 31" formed from superelastic material (e.g., NITINOL) and a first layer portion 37" formed from precipitation hardenable material (e.g., precipitation hardenable stainless steel).

Materials suitable for use in the practice of the invention are characterized in that they are precipitation hardenable by controlled heat treatment, not only to increase the ultimate tensile strength of the material but also to increase the tensile yield strength.

The characteristics of the composite elongate core member 11 according to the present invention, without any intention to limit the scope of the invention, may be described as follows:

The ultimate tensile strength and the Young modulus of elasticity for the composite elongated core member are proportional to the cross-sectional area of each constituent multiplied by the ultimate tensile strength or the modulus of elasticity, respectively, of that constituent, as defined in Equations I and II, respectively:

$$\sigma_{uts\,(C)}[\sigma_{uts\,(S)} \times (A_{(S)}/A_{(C)})] + [\sigma_{uts\,(Co)} \times (A_{(Co)}/A_{(C)})] \quad \text{Equation I}$$

$$E_{(C)} = [E_{(S)} \times (A_{(S)}/A_{(C)})] + [E_{(Co)} \times (A_{(Co)}/A_{(C)})] \quad \text{Equation II}$$

wherein $\sigma_{uts\,(C)}$ is the ultimate tensile strength,

E is the Young modulus of elasticity,

A is the cross sectional area,

C is the composite member,

Co is the core,

S is the shell (the shell may, itself, comprise various layers, such as the first and second layer portions).

The foregoing characteristics may be achieved by making the composite elongate core member 11, in part, from a precipitation hardenable material. Examples of such precipitation hardenable material include, but are not limited to, AISI (American Iron and Steel Institute) Type 600 series precipitation hardenable stainless steel. Additional examples include chromium-nickel based single stage martensitic precipitation hardenable stainless steel having modified proportions of chromium and nickel and with additional elements of copper and titanium, commercially available from Carpenter Steel Company of Reading, Pa., under the designation 455PH or 17-7PH; and a precipitation hardenable steel available under the trade designation 1RK91 from Sewden Steel.

Other suitable precipitation hardenable stainless steel include those which are essentially "nickel free" such as those sold under the designation BioDur 108, available from Carpenter's Specialty Alloys Operations, Reading, Pa. By way of example, the nominal composition of BioDur is chromium (21%), manganese (23%), nitrogen (1%), nickel (less than 0.3%) and iron (balance).

Other suitable precipitation hardenable material include cobalt based alloys such as those including nickel, cobalt, molybdenum and chromium, also commercially available under the designation MP35N (UNS (Unified Numbering System) R30035) available from Carpenter Steel Co. Also useful in the practice of the invention is a similar alloy that contains a small amount of iron (less than about 10%) and is commercially available under the trade designation Elgiloy (UNS R30003) and L605 as well as Haynes 242 from Haynes International of Kokomo, Ind. Haynes 242 is preferred due to its "friendly" properties that facilitate compatibility and bondability to NITINOL.

The material for forming the first layer portion 37 may be a superelastic alloy, such as superelastic NITINOL (NiTi).

By way of example, the ultimate tensile strength and Young modulus for the composite core member 11 according to FIG. 5, may be calculated using nominal and or preferred values for the ultimate tensile strength and Young modulus for each of the constituents, using Equations I and II, above, and the following parameters:

C has an overall outer diameter of 0.0125 inch,

Co is precipitation hardenable stainless steel (PHSS), $\%A_{(Co)}$=6 to 20%, nominal 12%-equivalent to a core outer diameter of about 0.0045 inch, S is superelastic NiTi, $\%A_{(S)}$=94 to 80%, nominal 88%, equivalent to a shell wall thickness of about 0.004 inch (0.008 inch total shell thickness), $E_{(Co)}$=28-30×10$^6$ psi, nominal 28.5×10$^6$ psi, for PHSS; and 33.5-35×10$^6$ psi, nominal 34.5×10$^6$ psi, for cobalt base alloys such as MP35N, L605, and Elgiloy, with less than 10% Iron, $\sigma_{uts(Co)}$=250-330 ksi, preferably ≧280 ksi, $E_{(S)}$=9-13×10$^6$ psi, nominal 12×10$^6$ for NiTi, $\sigma_{uts\,(S)}$=160-190 ksi, preferably ≧175 ksi, $\sigma uts_{(C)}$=[$\sigma_{uts\,(S)}$×($A_{(S)}/A_{(C)}$)]+[$\sigma uts_{(Co)}$×($A_{(Co)}/A_{(C)}$)], $\sigma uts_{(C)}$=(0.88×175 ksi)+(0.12×280 ksi)=188 ksi, $E_{(C)}$=(0.88×12×10$^6$ psi)+(0.12×28.5×10$^6$ psi)=14×10$^6$ psi As can be seen from the equations and numbers above, the elongate core members of the present invention will have an ultimate tensile strength and modulus of elasticity greater than the same for an identically dimensioned elongate member formed from superelastic NITINOL alone.

The composite elongate core member 11 will preferably have an ultimate tensile strength of at least 150 ksi, more preferably, at least 180 ksi, and most preferably, at least 200 ksi; and a modulus of elasticity greater than 9×10$^6$ psi, more preferably, greater than 12×10$^6$ psi, and most preferably, greater than 15×10$^6$ psi.

In another embodiment, the superelastic qualities of nickel-titanium alloys are preserved, yet the material's radiopacity is improved by addition of a ternary element. This is preferably accomplished by forming a composition consisting essentially of about 30 to about 52 percent titanium and the balance nickel and up to 10 percent of one or more additional ternary alloying elements. Such ternary alloying elements may be selected from the group consisting of iridium, platinum, gold, rhenium, tungsten, palladium, rhodium, tantalum, silver, ruthenium, and hafnium. In the preferred embodiment, the atomic percentage of platinum is greater than or equal to 2.5 and less than or equal to 15, preferably 42.8 atomic percent nickel, 49.7 atomic percent titanium, and 7.5 atomic percent platinum. In an alternative embodiment, the atomic percentage of palladium is greater than or equal to 2.5 and less than or equal to 20.

The minor addition of a quaternary element, for example, iron, to further enhance the alloy's formability or its thermomechanical properties is contemplated. The presence of impurities such as carbon or oxygen or the like is also possible.

The addition of the ternary element provides a guidewire with a first layer portion having improved radiopacity without increasing the layer thickness or core diameter. Increasing layer thicknesses detracts from the flexibility of the guidewire, which is detrimental to maneuverability. Rather, the guidewire with a superelastic NITINOL first layer with a ternary element added has a thin cross-sectional area akin to a conventional stainless steel guidewire and has comparable radiopacity to a stainless steel guidewire with a thin coating of gold.

Referring to FIG. 7, the guidewire 110 has a composite elongate core member 111 with a distal segment 113 having a distally tapered section 116. The distally tapered section 116 has a proximal portion 119, a distal portion 122, and a distal flexible section 125 at a distal end 128 of the guidewire 110 for negotiating the guidewire through the patient's vasculature without causing injury thereto. The distally tapered section 116 can be adjusted in length, taper angle, number of tapers and cross sectional shape to achieve the desired flexibility and performance characteristics for the guidewire 110.

The elongate core member 111 has an inner core element 131 formed from a precipitation hardenable material (e.g. Haynes 242) and a first layer portion 137 formed from superelastic NITINOL having a ternary element added and disposed on an outer surface 143 of the inner core element 131. The inner core element 131 is at least partially exposed at the distal flexible section 125 of the distal segment 113 of the composite elongate member 111. The inner core element 131 may also be exposed at a distal end 153 of the distal portion 122. The first layer portion 137 is at least partially exposed at the distal portion 122 of the distally tapered section 116 of the distal segment 113 of the composite elongate core member 111.

In the proximal portion 119 of the elongate core member 111, the first layer portion 131 provides exceptional radiopacity and superelastic properties. The Haynes 242 inner core element 131 provides increased stiffness, as compared to NITINOL, and, therefore, facilitates a smaller overall diameter guidewire.

In the distally tapered section 116 of the elongate core member 111, the first layer portion 137 provides great durability, elasticity and resistance to deformation in tortuous anatomy. The Haynes 242 inner core element 131 provides guidewire stiffness and torque performance.

At the distal end 153 of the distally tapered section 116 of the elongate core member 111, the Haynes 242 inner core element 131 provides guidewire stiffness and push, as well as shapeability and solderability.

In FIG. 7, the first layer portion 137 is shown as a smooth continuous layer. The inner core element 131 has a proximal section 155, a distal section 158 and a distal end 161. The first layer portion 137 has a distal section 164 and a proximal section 167.

The distal end 161 of the inner core element 131 may be secured to a distal end 176 of a flexible body 179 by a first body of solder 182. A proximal end 185 of the flexible body 179 may be secured to the distal section 164 of the first layer portion 137 with a second body of solder 188. The distal segment 113 of the elongate core member 111 may have several such tapered segments which may or may not be separated by segments of substantially constant diameter. The flexible body 179 may be disposed partially about the distally tapered section 116 of the distal segment 113 of the elongate core member 111. The distal flexible section 125 is shown as a flattened portion of the exposed inner core element 131, however, the distal flexible section can have a round cross section, or any other suitable configuration.

The guidewire 110 illustrated in FIG. 7 has several advantages. Increased stiffness is provided while maintaining elasticity and improving radiopacity. Additionally, an overall reduced diameter is facilitated. Moreover, a shapeable, core-to-tip is provided. It is contemplated that the dimensions of the guidewire 110 may be varied to meet almost any design criteria.

The following process is provided, by way of example and not as limitation, to illustrate the method of forming the composite elongate core member 11 of the guidewire 10 in accordance with the invention.

A NiTi alloy tube, for forming the first layer portion 37, having a composition of about 55.9% Ni and 44.1% Ti was drawn to a diameter of about 0.060 inch and an inner diameter of about 0.024 inch. A wire of 17-7PH precipitation hardenable stainless steel was formed with a diameter of about 0.020 inch for forming the inner core element 31. The 17-7PH wire was inserted into the first layer portion 37. A tube of 17-7PH was prepared with an inner diameter of about 0.068 inch and an outer diameter of about 0.114 inch for forming the second outer layer portion 46. The 17-7PH tube for the second layer portion 46 was disposed over the first layer portion 37 (NiTi tube) containing the inner core element 31 (17-7PH wire).

The entire assembly was then drawn in a series of five stages with a 30-60% reduction in cross-sectional area followed by a heat treatment between 600-800° C., in air for about 15 minutes, at each stage. The fifth stage was followed by a sixth stage which included drawing with cold work of about 16% followed by heat treating at a temperature between 400-600° C. and a seventh stage which included drawing with a cold work of about 50% but with no heat treatment. The final cold worked product was aged at a temperature of about 650° C. for about one minute to develop maximum bending, yield, and modulus with minimum springback.

It should be noted that other suitable methods may also be used. For example, the inner core element 31 and the first layer portion 37, and the second layer portion 46, may have different dimensions. Alternatively, the inner core element 31 may be loaded into the first layer portion 37 and cold drawn down to a suitable size prior to insertion into the second layer portion 46. The new assembly can then be drawn down to the desired final size.

In an alternative process, a NiTi alloy tube for the first layer portion 37 is provided with a ternary element added and the tube is drawn in a similar fashion. The tube is made by vacuum induction melting nickel and titanium with the ternary element according to the compositions desired. The ingot is then remelted for consistency. The ingot is next hot rolled into bar stock, then straightened and sized, and hot or cold formed into a cylinder. The cylinder is gun drilled to form the tubing. Instead of gun drilling, other methods of material removal known in the art may be used, including electric discharge machining (EDM), laser beam machining, and the like. Next, the tubing is cold drawn and annealed repeatedly to achieve the finished dimensions.

Referring to FIG. 8, the as-received core structure 150 of the preferred embodiment is shown. The Haynes 242 inner core 131 is housed in a shell 137 made of NITINOL and a ternary element as described above. The dash lines in FIG. 8 illustrate how the core structure may be ground to provide the guidewire 110, illustrated in FIG. 7.

Any of the foregoing preferred embodiment steps may be repeated, taken out of sequence, or omitted as necessary depending on desired results. From here on, the tube follows the previously defined drawn filled tube process.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A guidewire comprising:
a composite elongated guidewire core formed at least in part from a precipitation hardenable material having a Young's Modulus of about 33.5 to $35 \times 10^6$ psi and at least in part from a superelastic nickel-titanium alloy including a ternary element selected from the group consisting of iridium, platinum, gold, rhenium, tungsten, palladium, rhodium, tantalum, silver, ruthenium and halfnium; and
wherein the precipitation hardenable material is a cobalt based precipitation hardenable alloy.

2. The guidewire of claim 1, wherein the cobalt based alloy further includes nickel, molybdenum and chromium.

3. The guidewire of claim 2, wherein the alloy further includes less than about 10% by wt. iron.

4. The guidewire of claim 1, wherein the nickel-titanium alloy comprises at least 2.5 atomic percent and less than or equal to 15 atomic percent platinum.

5. The guidewire of claim 1, wherein the nickel-titanium alloy comprises at least 2.5 atomic percent and less than or equal to 20 atomic percent palladium.

6. The guidewire of claim 1, wherein the superelastic nickel-titanium alloy is comprised of about 30 to about 52 percent titanium, up to 10 percent of one or more ternary elements and the balance nickel.

7. The guidewire of claim 6, wherein the superelastic nickel-titanium alloy is comprised of 42.8 atomic percent nickel, 49.7 atomic percent titanium and 7.5 atomic percent platinum.

8. The guidewire of claim 1, wherein the superelastic nickel-titanium alloy includes a quaternary element.

9. The guidewire of claim 8, wherein the quaternary element is iron.

10. The guidewire of claim 1, wherein the elongate member is a guide wire.

11. A guidewire comprising:
a composite elongate core, the elongate core having an inner core element and a first layer portion disposed at least in part about the inner core element, the inner core element formed from precipitation hardenable material and the first layer portion formed from a superelastic nickel-titanium alloy including a ternary element selected from the group consisting of iridium, platinum, gold, rhenium, tungsten, palladium, rhodium, tantalum, silver, ruthenium and halfnium; and
wherein the precipitation hardenable material is a cobalt based precipitation hardenable alloy that includes at least one of nickel, molybdenum, and chromium.

12. The guidewire of claim 11, wherein the composite elongate core includes a distal segment having a distally tapered section with proximal and distal portions, and a distal flexible section, the inner core element being at least partially exposed at the distal flexible section of the distal segment of the composite elongate member.

13. A guidewire comprising:
a composite elongate core, the elongate core having an inner core element and a first layer portion disposed at least in part about the inner core element, the inner core element formed from precipitation hardenable material wherein the precipitation hardenable material is a cobalt based precipitation hardenable alloy, and the first layer portion formed from superelastic nickel-titanium alloy including a ternary element selected from the group consisting of iridium, platinum, gold, rhenium, tungsten, palladium, rhodium, tantalum, silver, ruthenium and halfnium.

14. A method of making an elongated guidewire core, comprising:
providing a tube including a superelastic nickel-titanium alloy and a ternary element selected from the group of elements consisting of iridium, platinum, gold, rhenium, tungsten, palladium, rhodium, tantalum, silver, ruthenium and halfnium;
cold drawing the tube;
inserting a wire having a precipitation hardenable material into the tube;
cold drawing the tube and wire;
heat treating the tube and wire; and
wherein the tube is radiopaque.

15. The method of claim 14, wherein the step of providing an elongated core includes melting nickel, titanium, and the ternary element, cooling to form an alloy ingot, hot forming the alloy ingot, forming the alloy ingot into a cylinder, drawing the cylinder, and annealing the cylinder.

16. The method of claim 14, wherein the atomic percent of platinum is greater than or equal to about 2.5 and less than or equal to about 15.

17. The method of claim 14, wherein the atomic percent of palladium is greater than or equal to about 2.5 and less than or equal to about 20.

18. The method of claim 14, wherein the alloy includes a quaternary element.

* * * * *